United States Patent [19]

Jaedicke et al.

[11] Patent Number: 4,493,802

[45] Date of Patent: Jan. 15, 1985

[54] PREPARATION OF O,O'-DITHIODIBENZOIC ACIDS

[75] Inventors: Hagen Jaedicke, Ludwigshafen; Peter Tonne, Neustadt, both of Fed. Rep. of Germany

[73] Assignee: BASF Aktiengesellschaft, Ludwigshafen, Fed. Rep. of Germany

[21] Appl. No.: 455,806

[22] Filed: Jan. 5, 1983

[30] Foreign Application Priority Data

Jan. 22, 1982 [DE] Fed. Rep. of Germany ....... 3201904

[51] Int. Cl.$^3$ ................. C07C 143/52; C07C 149/40
[52] U.S. Cl. ................... 260;507 R; 562/432
[58] Field of Search ..................... 260/507 R; 562/432

[56] References Cited

U.S. PATENT DOCUMENTS 2,064,395 12/1936 Tschunkur et al. ................. 562/432

FOREIGN PATENT DOCUMENTS 6930 8/1907 United Kingdom ................ 562/432

Primary Examiner—Nicky Chan
Attorney, Agent, or Firm—John H. Shurtleff

[57] ABSTRACT o,o'-Dithiodibenzoic acids are prepared by a process wherein a diazotized anthranilic acid or anthranilate is reacted with sulfur dioxide in the presence of an acid, water and a copper salt, and if desired in the presence of an alkali metal iodide, in a 1st stage at from 20° to 50° C. and then in a 2nd stage at from 80° to 100° C.

The o,o'-dithiodibenzoic acids obtainable by the process of the invention are useful starting materials for the preparation of crop protection agents, dyes and drugs.

20 Claims, No Drawings

PREPARATION OF O,O′-DITHIODIBENZOIC ACIDS

The present invention relates to a process for the preparation of o,o′-dithiodibenzoic acids by reacting a diazotized anthranilic acid or anthranilate with sulfur dioxide in the presence of an acid, water and a copper salt, and if desired in the presence of an alkali metal iodide, in a 1st stage at from 20° to 50° C. and then in a 2nd stage at from 80° to 100° C.

The o,o′-dithiodibenzoic acids are prepared by decomposing the diazonium salt of the anthranilic acid in aqueous sodium disulfide solution (Org. Synth. Coll. Vol. II, pages 580–583 (1943)). In this process, the presence of a sulfide and elementary sulfur means that substantial expense is involved in keeping the effluent and waste gases free from toxic hydrogen sulfide.

Meerwein, Chem. Ber. 90 (1957), 847, shows that diazotized anthranilic acid may be reacted with sulfur dioxide in glacial acetic acid to give a 51% yield of o,o′-dithiodibenzoic acid. When this process is carried out industrially on a large scale, the acetic acid is as a rule lost.

It is an object of the present invention to provide a process for the preparation of o,o′-dithiodibenzoic acids which avoids the disadvantages described.

We have found that this object is achieved, and that o,o′-dithiodibenzoic acids of the formula

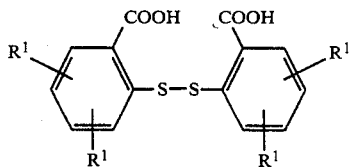

where the individual radicals $R^1$ may be identical or different and are each hydrogen, halogen, nitro, —SO$_3$H or an aliphatic radical, are advantageously obtained by reaction of a diazotized anthranilic acid derivative with sulfur dioxide in the presence of an acid, water and a catalyst for destroying the diazonium salt, if a diazonium salt of an anthranilic acid of the formula

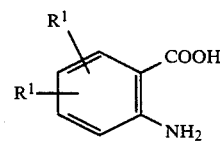

or a diazonium salt of an anthranilate of the formula

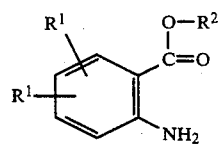

where $R^1$ has the above meanings and $R^2$ is an aliphatic radical, is reacted in the presence of a copper salt, and if desired in the presence of an alkali metal iodide, in a 1st stage at from 20° to 50° C. and then in a 2nd stage at from 80° to 100° C.

Where the diazonium chloride of anthranilic acid is used, the reaction can be represented by the following equation:

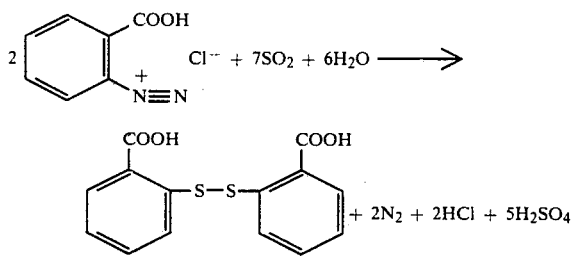

In comparison with the conventional processes, the process according to the invention gives o,o′-dithiodibenzoic acids in better yield and purity and by a simpler and cheaper route. It produces substantially less pollution than the process employing a sulfide and elementary sulfur, since no hydrogen sulfide, elementary sulfur or polysulfides are formed, and accordingly no substantial problems regarding effluent and waste gases arise. Moreover, filtration problems which result from the presence of elementary sulfur are avoided, and no organic substances, eg. glacial acetic acid, are lost. All these advantageous results are surprising in view of the prior art.

The diazonium salt of starting material II or III and sulfur dioxide can be employed in stoichiometric amounts, but it is advantageous to use from 3.5 to 10, in particular from 3.5 to 4.5, moles of SO$_2$ per mole of starting material II or III. Preferred starting materials II and III, and accordingly preferred end products I, are those of the formulae where the individual radicals $R^1$ may be identical or different and are each hydrogen, nitro, —SO$_3$H, bromine or, in particular, chlorine, or alkyl of 1 to 6 carbon atoms, and $R^2$ is alkyl of 1 to 8 carbon atoms. The above radicals may be further substituted by groups which are inert under the reaction conditions, eg. alkyl or alkoxy of 1 to 4 carbon atoms. If starting materials III are reacted, the ester groups are also destroyed during the decomposition of the diazonium salt, so that the end product I is again obtained.

Thus, examples of suitable starting materials II are the diazonium salts of anthranilic acid which is unsubstituted or monosubstituted in the 3-, 4-, 5- or 6-position or disubstituted in the 3,4-, 3,5-, 3,6-, 4,5- or 5,6-position by identical or different substituents, examples of suitable substituents being bromine, chlorine, methyl, ethyl, propyl, isopropyl, butyl, sec.-butyl, isobutyl and tert.-butyl.

Examples of suitable starting materials III are the diazonium salts of ethyl, propyl, isopropyl, butyl, sec.-butyl, isobutyl and tert.-butyl anthranilates which are unsubstituted or monosubstituted or disubstituted by the above substituents.

The diazotization is carried out in a conventional manner, for example by reacting the starting material with sodium nitrite in an aqueous solution containing hydrochloric acid, at 0°–10° C., for example for from 5 to 70 minutes. While it is advantageous to employ equimolar amounts of anthranilic acid and the nitrite, the amount of hydrochloric acid can vary within wide limits. However, in large-scale industrial production, it is advantageous to employ from 1 to 3, preferably from 1 to 2, moles of HCl per mole of anthranilic acid. Accordingly, it is also possible to employ other acids instead of hydrochloric acid, for example sulfuric acid or phosphoric acid. Diazonium chlorides and sulfates are particularly preferred. Residual nitrite may then advantageously be destroyed by the addition of urea.

The reaction is carried out in 2 stages, the 1st stage at from 20° to 50° C., preferably from 30° to 40° C., and the 2nd stage at from 80° to 100° C., preferably from 90° to 100° C., under atmospheric or superatmospheric pressure, continuously or batchwise. It is advantageous to use a ready-prepared diazotization solution directly in the 1st stage of the reaction according to the invention. From 60 to 90, in particular from 70 to 80, % by weight of water, based on the weight of starting material II or III, is advantageously present during the diazotization stage as well as during both stages of the reaction. It is likewise advantageous to employ from 0.5 to 5 moles of acid per mole of starting material II or III for stages 1 and 2.

Copper salts are added, if desired together with other substances, as catalysts for accelerating the decomposition in the 1st stage. The salts may be copper(I) or, advantageously, copper(II) salts, suitable examples being copper(II) acetate, copper(II) bromide and copper(II) chloride, and the corresponding copper(I) salts. Copper(II) chloride is preferred.

Advantageously from 0.005 to 0.05, preferably from 0.01 to 0.02, mole of copper salt is employed per mole of starting material II or III.

It is advantageous to use an alkali metal iodide as an additional decomposition catalyst, and this is advantageously employed in an amount of from 0.005 to 0.05 mole per mole of starting material II or III.

The reaction may be carried out as follows: the diazonium solution is prepared in a conventional manner, and excess nitrous acid is destroyed, if required, with urea. The metal salt, and advantageously the alkali metal iodide, are then added, and the mixture is brought to 20°–50° C., in particular 30°–40° C., this being the decomposition temperature of the 1st stage. The residence times are advantageously from 1 to 3 hours in the 1st stage, and from 0.1 to 2 hours in the second stage. Sulfur dioxide is then advantageously passed in, and the 2nd stage of the decomposition is carried out with the above components and in the above residence time. The passage of $SO_2$ into the mixture may be continued during either a part of the 2nd stage or its entirety. However, the total amount of $SO_2$ for the reaction of both stages is advantageously added during the 1st stage. As a rule, from 3.5 to 7 moles of sulfur dioxide, advantageously from 2 to 6 moles in the 1st stage and from 0 to 3 moles in the 2nd stage, are passed in per mole of starting material II or III. The temperature may be increased continuously in the 2nd stage, or, in each stage, the mixture may be kept at one or more of the above temperatures for the entire residence time in this stage, or for a part of this time. For example, the temperature may be increased stepwise from 20° to 100° C.

In order that the diazonium salt does not decompose too vigorously, the reaction mixture is heated to no more than 50° C. in stage 1. In a preferred embodiment, a stream of from 2 to 4.5 moles of sulfur dioxide per mole of starting material II or III is passed into the reaction mixture. The latter is then heated to 80°–100° C., and from 0 to 2 moles of sulfur dioxide per mole of starting material II or III are passed in during stage 2. During this procedure, the o,o'-dithiodibenzoic acid is precipitated from the initially clear solution in the 2nd stage. The reaction in this stage is advantageously carried out for from 20 to 55 minutes at from 80° to 100° C. The product is filtered off, and dried under reduced pressure. In another embodiment, the diazonium solution is added to the copper salt solution while $SO_2$ is being passed in.

The o,o'-dithiodibenzoic acids obtainable by the process of the invention are useful starting materials for the preparation of crop protection agents, dyes and drugs, and may be used to prepare saccharins. Regarding the use of these compounds, reference may be made to U.S. Pat. Nos. 2,705,242 and 2,667,503.

EXAMPLE 1

14.4 g of anthranilic acid were suspended in 70 g of water and 18 g of 30% strength hydrochloric acid, and 29.4 g of a 25% strength aqueous sodium nitrite solution was added while cooling with ice, the addition being carried out in such a manner that the internal temperature did not exceed 5° C. After the addition was complete, the mixture was stirred for 5 minutes at 0° C., and excess nitrous acid was destroyed with 1 g of urea. The diazonium solution was cooled to 0° C. and then added, in the course of 1 hour, to 0.4 g of a 50% strength aqueous solution of copper(II) chloride.$2H_2O$ at 35° C. While the diazonium solution was being added, a stream of 18.4 g of $SO_2$ per hour was passed into the reaction vessel, the temperature being kept at 35° C. After the reaction had proceeded for 60 minutes at 35°, the $SO_2$ stream was reduced to 16.4 g of $SO_2$ per hour, and at the same time the mixture was heated to the reflux temperature (98° C.) in the course of 30 minutes. When 98° C. was reached, the passage of $SO_2$ was discontinued. The residence time (from the beginning of the reaction) was 70 minutes in total in the 1st stage, and 40 minutes in the 2nd stage. As early as two hours after the beginning of decomposition (beginning of the 1st stage), the yield of o,o'-dithiodibenzoic acid was 90% of theory. The mixture was cooled to 50° C. and filtered, the filter cake was dried for 2 hours at 100° C. under reduced pressure, and 14.5 g (94.8% of theory) of product of melting point 286°–288° C. were obtained.

EXAMPLE 2

137.5 g of anthranilic acid were dissolved in 500 g of water and 134 g of 30% strength hydrochloric acid, and the solution was cooled to 5° C. 241 g of a 30% strength $NaNO_2$ solution were added to the stirred solution in such a manner that the internal temperature did not exceed 5° C. 6 g of a 50% strength aqueous solution of Cu(II) $Cl_2.2H_2O$ and 1.6 g of potassium iodide in 100 g of water were initially taken in a stirred vessel, and the previously prepared solution of the diazonium salt of the anthranilic acid was pumped, in the course of one hour, into the decomposition vessel. From the beginning of the addition of diazonium solution, a stream of 184 g/hour of $SO_2$ was passed into the decomposition vessel, whose internal temperature was kept at 30° C. from the beginning, by cooling. After all the diazonium salt solution had been introduced (a procedure which took 60 minutes), the $SO_2$ stream was reduced to 130 g/hour, and after 90 minutes (from the beginning) the passage of $SO_2$ was discontinued. The mixture was then heated to the reflux temperature (99° C.) in the course of 30 minutes. The residence time (from the beginning of the reaction) was 1.7 hours in total in the 1st stage, and 0.7 hour in the 2nd stage. The mixture was kept at 99° C. for 20 minutes, cooled to 40° C. in the course of 20 minutes, and then filtered. 143.8 g (94% of theory) of o,o'-dithiodibenzoic acid of melting point 286°–288° C. were obtained.

We claim:

1. In a process for the preparation of o,o'-dithiodibenzoic acid of the formula

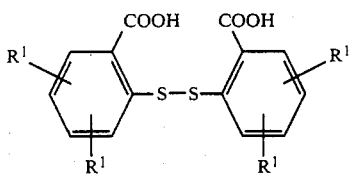

where the individual radicals $R^1$ may be identical or different and are each hydrogen, halogen, nitro, —$SO_3H$ or alkyl of 1 to 6 carbon atoms, by reaction of a diazotized anthranilic acid derivative with sulfur dioxide in the presence of an acid, water and a catalyst for destroying the diazonium salt, the improvement which comprises:

reacting a diazonium salt of an anthranilic acid of the formula

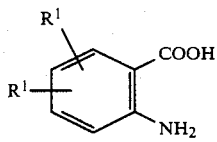

or a diazonium salt of an anthranilate of the formula

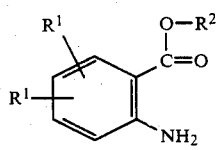

where $R^1$ has the above meanings and $R^2$ is alkyl of 1 to 8 carbon atoms, with said sulfur dioxide in the presence of said acid and water and in the presence of a copper salt as the essential catalyst destroying the diazonium salt in a 1st stage at from 20° to 50° C. and then in a 2nd stage at from 80° to 100° C.

2. A process as claimed in claim 1, wherein the reaction is carried out using from 3.5 to 10 moles of $SO_2$ per mole of starting material II or III.

3. A process as claimed in claim 1, wherein the reaction is carried out using from 1 to 3 moles of HCl per mole of anthranilic acid.

4. A process as claimed in claim 1, wherein the reaction in the 1st stage is carried out at from 30° to 40° C.

5. A process as claimed in claim 1, wherein the reaction in the 2nd stage is carried out at from 90° to 100° C.

6. A process as claimed in claim 1, wherein the reaction is carried out using from 60 to 90% by weight, based on the weight of starting material II or III, of water.

7. A process as claimed in claim 1, wherein the reaction is carried out using from 0.5 to 5 moles of acid per mole of starting material II or III.

8. A process as claimed in claim 1, wherein the reaction is carried out using 0.005 to 0.05 mole of copper salt per mole of starting material II or III.

9. A process as claimed in claim 1, wherein the residence time in the 1st stage is from 1 to 3 hours, and the residence time in the second stage is from 0.1 to 2 hours.

10. A process as claimed in claim 1, wherein, per mole of starting material II or III, from 2 to 6 moles of sulfur dioxide are employed for the reaction in the 1st stage and from 0 to 3 moles are employed for the reaction in the 2nd stage.

11. A process as claimed in claim 1, wherein the reaction is carried out in the presence of an alkali metal iodide.

12. A process as claimed in claim 11, wherein the reaction is carried out using from 0.005 to 0.05 mole of alkali metal iodide per mole of starting material II or III.

13. A process as claimed in claim 1, wherein the reaction is carried out using from 3.5 to 7 moles of $SO_2$ per mole of starting material II or III.

14. A process as claimed in claim 1, wherein the reaction is carried out in the presence of an acid selected from the group consisting of hydrochloric acid, sulfuric acid and phosphoric acid.

15. A process as claimed in claim 1, wherein the reaction is carried out using from 1 to 2 moles of HCl per mole of anthranilic acid.

16. A process as claimed in claim 1, wherein the reaction is carried out using 0.01 to 0.02 mole of copper salt per mole of starting material II or III.

17. A process as claimed in claim 1, wherein the reaction is carried out in the presence of a copper salt selected from the group consisting of copper(II) acetate, copper(II) bromide and copper(II) chloride.

18. A process as claimed in claim 1, wherein the reaction is carried out using from 3.5 to 4.5 moles of sulfur dioxide per mole of starting material II or III.

19. A process as claimed in claim 1, wherein the reaction is carried out using
 (a) about 3.5 to 10 moles of $SO_2$,
 (b) about 0.5 to 5 moles of an acid selected from the group consisting of hydrochloric acid, sulfuric acid and phosphoric acid,
 (c) about 60 to 90% by weight of water, and
 (d) about 0.005 to 0.05 mole of the copper salt, all moles and percentages being per mole and percentage by weight, respectively, of starting material II or III.

20. A process as claimed in claim 19, wherein the reaction is carried out in the presence of 0.005 to 0.05 mole of alkali metal iodide per mole of starting material II or III.

* * * * *